United States Patent [19]
Shimabukuro

[11] Patent Number: 5,718,578
[45] Date of Patent: Feb. 17, 1998

[54] DENTAL IMPRESSION TRAY

[76] Inventor: Cindy M. Shimabukuro, 16725 NE 91st St., Redmond, Wash. 98052

[21] Appl. No.: 762,296

[22] Filed: Dec. 9, 1996

[51] Int. Cl.$^6$ .................................................. A61C 9/00
[52] U.S. Cl. ..................................... 433/37; 433/40
[58] Field of Search ............................ 433/37, 40, 48, 433/214

[56] References Cited

U.S. PATENT DOCUMENTS

| | | | |
|---|---|---|---|
| 883,592 | 3/1908 | Trigger | 433/40 |
| 1,367,627 | 2/1921 | Roach | 433/37 |
| 1,410,311 | 3/1922 | Howe | 433/40 |
| 1,505,684 | 8/1924 | Ainsworth | 433/40 |
| 2,450,591 | 10/1948 | Hawkinson | 433/40 |

*Primary Examiner*—John J. Wilson

[57] ABSTRACT

A new Dental Impression Tray for making a dental impression of a lingual surface or a buccal surface of a tooth. The inventive device includes a tray portion and a handle portion extending from the tray portion, wherein the tray portion is perpendicularly removable from the lingual surface or the buccal surface of the tooth. The tray portion is adapted to retain a dental impression compound for use in making the dental impression. The tray portion comprises a first wall, and a second wall joined perpendicular to the first wall whereby the first wall and the second wall form a trough at an intersection thereof for retaining the dental impression compound.

13 Claims, 3 Drawing Sheets

DENTAL IMPRESSION TRAY

BACKGROUND OF THE INVENTION

1. Field of the Invention

The present invention relates to dental trays and more particularly pertains to a new Dental Impression Tray for making a dental impression of a lingual surface or a buccal surface of a tooth.

2. Description of the Prior Art

The use of dental trays is known in the prior art. More specifically, dental trays heretofore devised and utilized are known to consist basically of familiar, expected and obvious structural configurations, notwithstanding the myriad of designs encompassed by the crowded prior art which have been developed for the fulfillment of countless objectives and requirements.

Known prior art dental trays include U.S. Pat. No. 5,336,086; U.S. Pat. No. 5,340,308; U.S. Pat. No. 4,689,010; U.S. Pat. No. 5,135,392; U.S. Pat. No. 4,146,963 and U.S. Pat. No. 3,978,585.

While these devices fulfill their respective, particular objectives and requirements, the aforementioned patents do not disclose a new Dental Impression Tray. The inventive device includes a tray portion and a handle portion extending from the tray portion, wherein the tray portion is perpendicularly removable from a lingual surface or a buccal surface of a tooth.

In these respects, the Dental Impression Tray according to the present invention substantially departs from the conventional concepts and designs of the prior art, and in so doing provides an apparatus primarily developed for the purpose of making a dental impression of a lingual surface or a buccal surface of a tooth.

SUMMARY OF THE INVENTION

In view of the foregoing disadvantages inherent in the known types of dental trays now present in the prior art, the present invention provides a new Dental Impression Tray construction wherein the same can be utilized for making a dental impression of a lingual surface or a buccal surface of a tooth.

The general purpose of the present invention, which will be described subsequently in greater detail, is to provide a new Dental Impression Tray apparatus and method which has many of the advantages of the dental trays mentioned heretofore and many novel features that result in a new Dental Impression Tray which is not anticipated, rendered obvious, suggested, or even implied by any of the prior art dental trays, either alone or in any combination thereof.

To attain this, the present invention generally comprises a tray portion and a handle portion extending from the tray portion, wherein the tray portion is perpendicularly removable from a lingual surface or a buccal surface of a tooth.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new Dental Impression Tray apparatus and method which has many of the advantages of the dental trays mentioned heretofore and many novel features that result in a new Dental Impression Tray which is not anticipated, rendered obvious, suggested, or even implied by any of the prior art dental trays, either alone or in any combination thereof.

It is another object of the present invention to provide a new Dental Impression Tray which may be easily and efficiently manufactured and marketed.

It is a further object of the present invention to provide a new Dental Impression Tray which is of a durable and reliable construction.

An even further object of the present invention is to provide a new Dental Impression Tray which is susceptible of a low cost of manufacture with regard to both materials and labor, and which accordingly is then susceptible of low prices of sale to the consuming public, thereby making such Dental Impression Tray economically available to the buying public.

Still yet another object of the present invention is to provide a new Dental Impression Tray which provides in the apparatuses and methods of the prior art some of the advantages thereof, while simultaneously overcoming some of the disadvantages normally associated therewith.

Still another object of the present invention is to provide a new Dental Impression Tray for making a dental impression of a lingual surface or a buccal surface of a tooth.

Yet another object of the present invention is to provide a new Dental Impression Tray which includes a tray portion and a handle portion extending from the tray portion, wherein the tray portion is perpendicularly removable from a lingual surface or a buccal surface of a tooth.

Still yet another object of the present invention is to provide a new Dental Impression Tray that can be removed perpendicularly from a lingual surface or a buccal surface of a tooth.

Even still another object of the present invention is to provide a new Dental Impression Tray that protects against damage to a dental impression of a lingual surface or a buccal surface of a tooth which may occur when lifting a traditional dental tray straight up while making a lower dental impression or when pulling a traditional dental tray straight down while making an upper dental impression.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
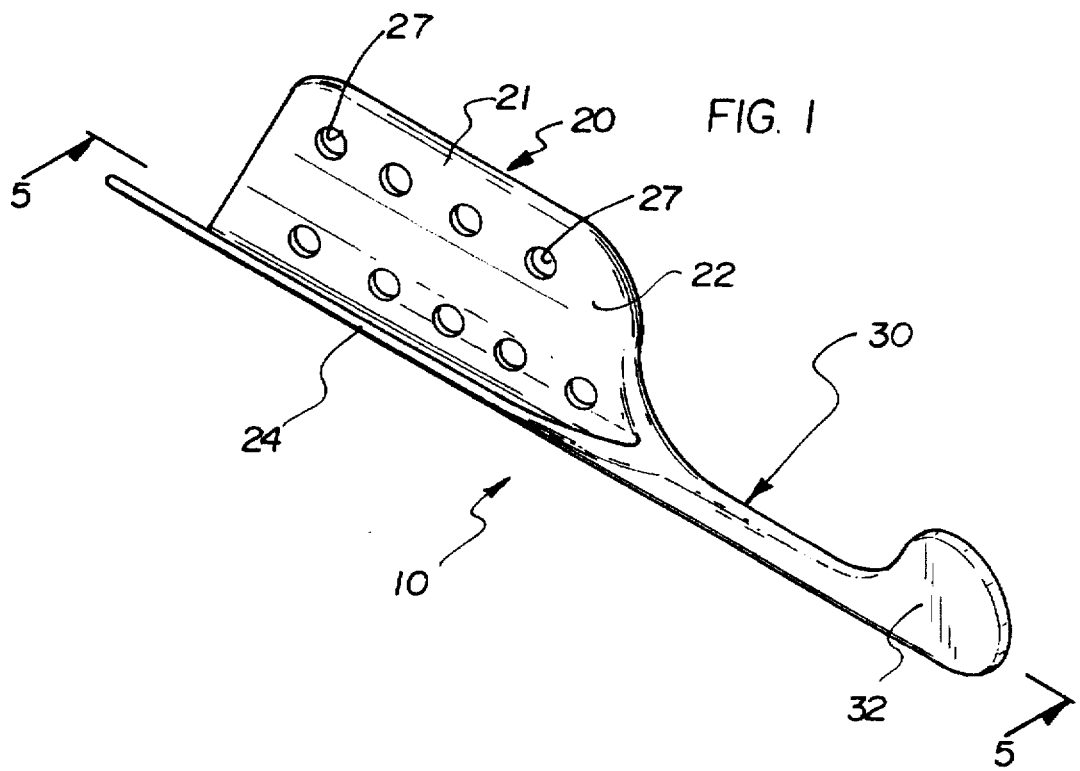
FIG. 1 is an illustration of a new Dental Impression Tray according to the present invention.
Figure 2:
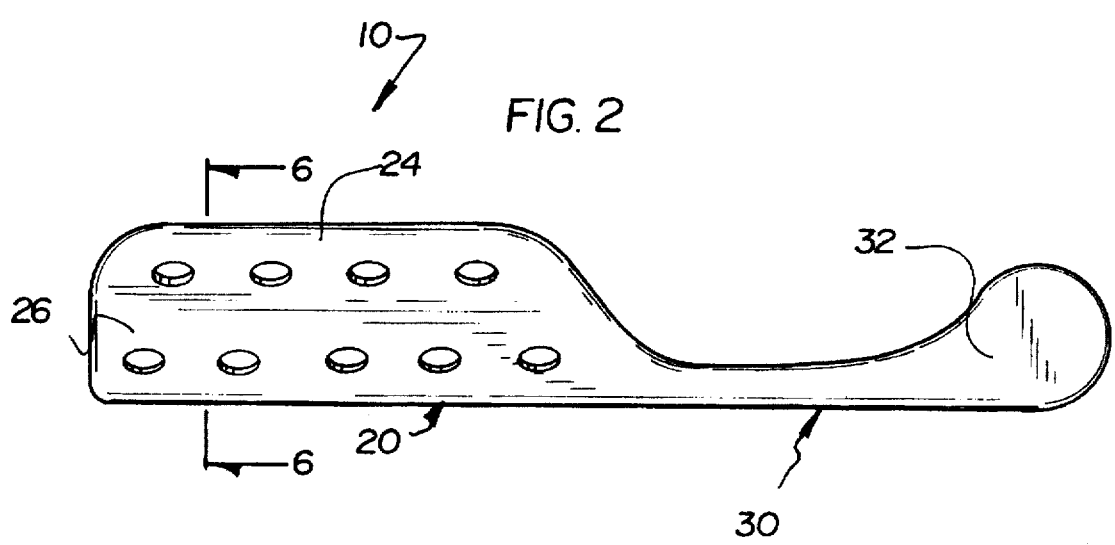
FIG. 2 is a side view of the present invention.

With reference now to the drawings, and in particular to FIGS. 1 through 6 thereof, a new Dental Impression Tray embodying the principles and concepts of the present invention and generally designated by the reference numeral 10 will be described.

More specifically, it will be noted that the Dental Impression Tray 10 comprises a tray portion 20 and a handle portion 30 extending from the tray portion 20, wherein the tray portion 20 is perpendicularly removable from a lingual surface 3 or a buccal surface 4 of a tooth 2. The Dental Impression Tray 10 is generally intended for use in making a dental impression of a decayed area 6 of the tooth 2 after the decayed area 6 has been prepared by a dentist.

Figure 3:
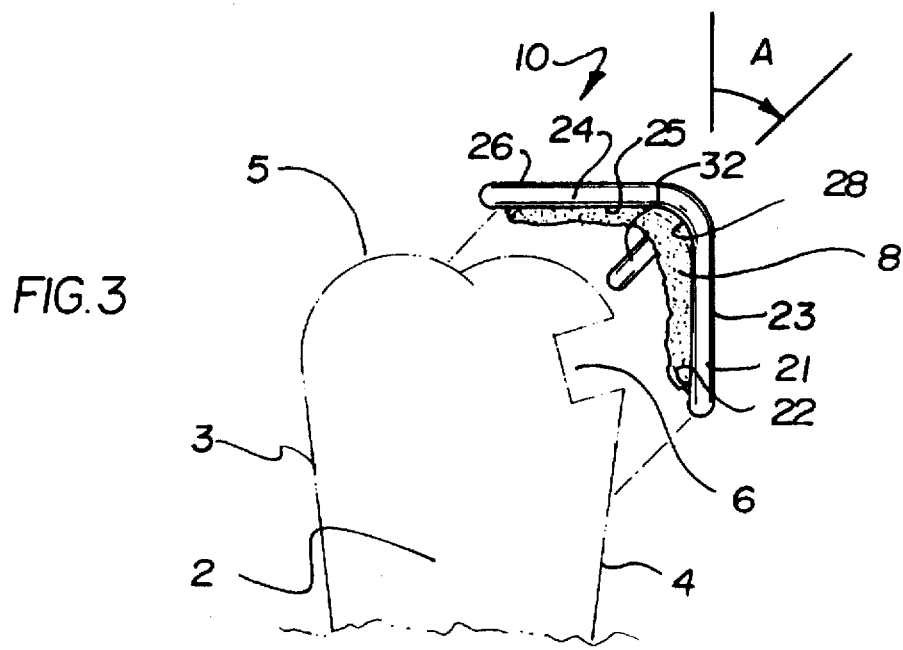
FIG. 3 is an end view of the present invention in use.
Figure 6:
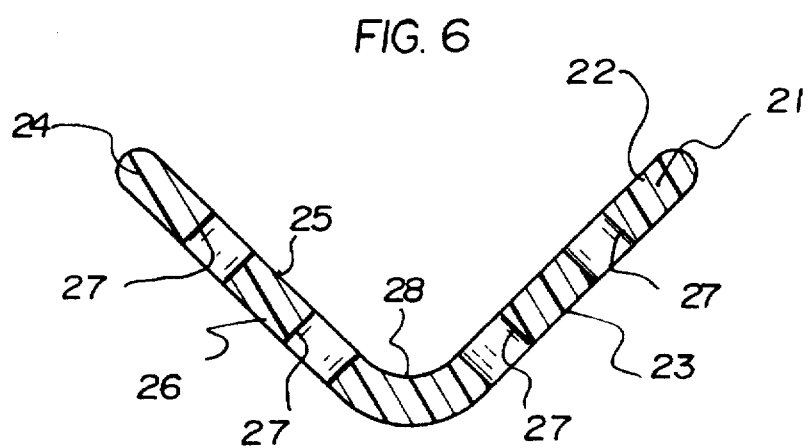
FIG. 6 is a cross sectional view taken along line 6—6 of FIG. 2.

As best illustrated in FIGS. 3 and 6, it can be shown that the tray portion 20 comprises a first wall 21 and a second wall 24. The first wall 21 has an inner surface 22 and an outer surface 23 and the second wall 24 has an inner surface 25 and an outer surface 26. The first wall 21 and the second wall 24 are joined perpendicular to each other whereby the inner surface 22 of the first wall 21 and the inner surface 25 of the second wall 24 form a trough 28 at an intersection of the first wall 21 and the second wall 24.

Figure 4:
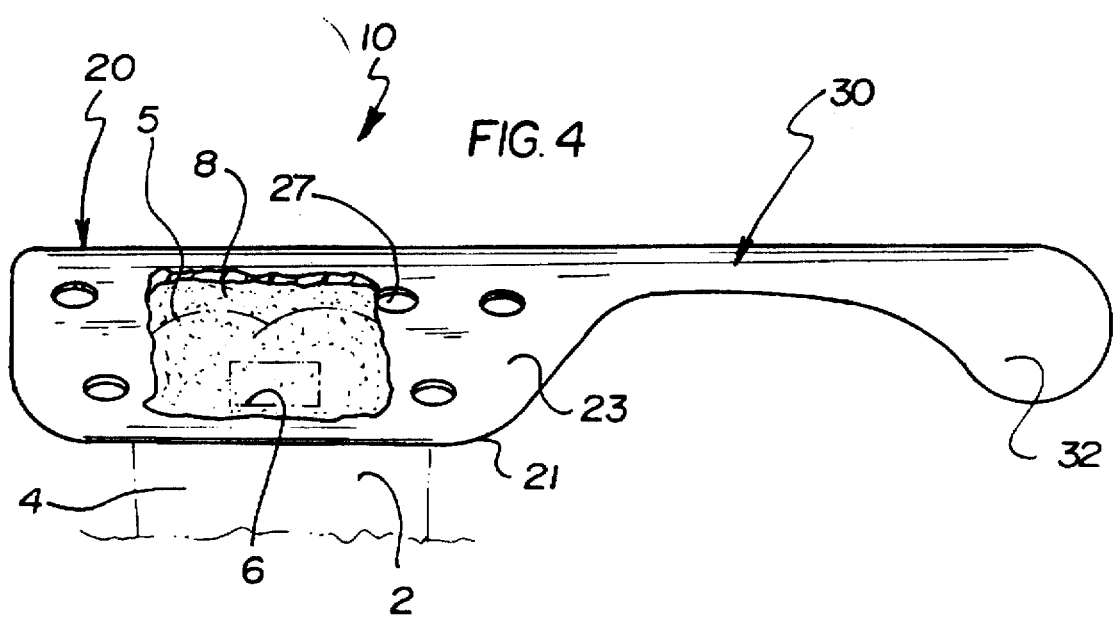
FIG. 4 is a cut-away side view of the present invention in use.
Figure 5:
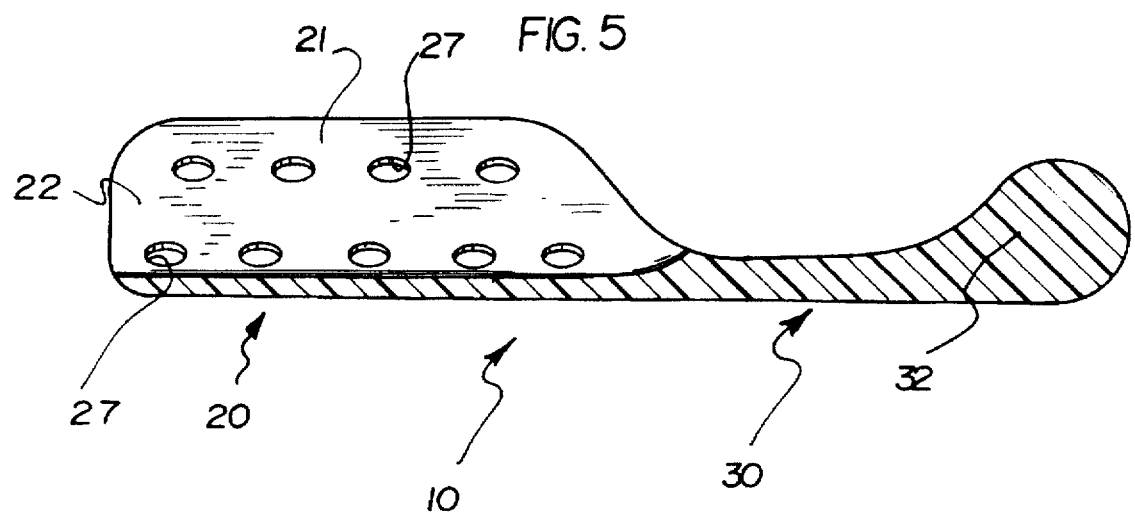
FIG. 5 is a cross sectional view taken along line 5—5 of FIG. 1.

As best illustrated in FIGS. 3 and 4, it can be shown that the first wall 21 and the second wall 24 of the tray portion 20 are positionable adjacent the buccal surface 4 of the tooth 2 and the masticatory (or occlusal) surface 5 of the tooth 2 and removable perpendicularly from the buccal surface 4 of the tooth 2. The first wall 21 and the second wall 24 of the tray portion 20 are positionable adjacent the lingual surface 3 of the tooth 2 and the masticatory surface 5 of the tooth 2 and removable perpendicularly from the lingual surface 3 of the tooth 2. Preferably, as best illustrated in FIG. 3, the tray portion 20 is angularly removable from the masticatory surface 5 and the buccal surface 4 of the tooth 2 when positioned adjacent thereto and, alternatively, is angularly removable from the masticatory surface 5 and the lingual surface 3 of the tooth 2 when positioned adjacent thereto. Ideally, the tray portion 20 is removable at an angle generally perpendicular to the decayed area 6.

As best illustrated in FIGS. 3 and 4, it can be shown that the tray portion 20 is adapted to retain a dental impression compound 8 for use in making a dental impression. The dental impression compound 8 is disposed on the inner surface 22 of the first wall 21, on the inner surface 25 of the second wall 24, and in the trough 28. The first wall 21 and the second wall 24 have a plurality of holes 27 therethrough for retaining the dental impression compound 8.

As best illustrated in FIGS. 1 through 4, it can be shown that a lobe 32 for grasping the handle portion 30 is provided at an end of the handle portion 30 distal the tray portion 20. The lobe 32 is rotated laterally along a longitudinal axis of the handle portion 30 at an angle A from a lateral axis of the first wall 21 toward a lateral axis of the second wall 24. The angle of rotation is about 45 degrees.

In use, a dental impression compound 8 is disposed on the inner surface 22 of the first wall 21, on the inner surface 25 of the second wall 24, and in the trough 28 formed by the intersection of the first wall 21 and the second wall 24. A user grasps the lobe 32 provided at the end of the handle portion 30 and the first wall 21 and the second wall 24 of the tray portion 20 are positioned adjacent the buccal surface 4 of a tooth 2 and the masticatory surface 5 of the tooth 2 or the first wall 21 and the second wall 24 of the tray portion 20 are positioned adjacent the lingual surface 3 of a tooth 2 and the masticatory surface 5 of the tooth 2. After a dental impression is made, the tray portion 20 is removed perpendicularly from the lingual surface 3 or the buccal surface 4 of the tooth 2.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A Dental Impression Tray for use in making a dental impression of a tooth with a dental impression compound, comprising:

a tray portion including a first wall and a second wall joined and generally perpendicularly oriented to each other, said tray portion adapted to retain a quantity of said dental impression compound; and an elongated handle portion extending from said tray portion along a common axis of said first wall and said second wall thereof, whereby said tray portion is simultaneously positionable adjacent and substantially parallel to an occlusal surface and a lingual surface of said tooth and is angularly removable from said lingual surface of said tooth, and whereby said tray portion is simultaneously positionable adjacent and substantially parallel to said occlusal surface and a buccal surface of said tooth and is angularly removable from said buccal surface of said tooth.

2. The Dental Impression Tray of claim 1, wherein said first wall and said second wall each have an inner surface and an outer surface, said inner surface of said first wall and said inner surface of said second wall forming a trough at an intersection of said first wall and said second wall, said trough extending along substantially an entire length of said first wall and said second wall.

3. The Dental Impression Tray of claim 1, wherein said first wall and said second wall of said tray portion each have a plurality of holes therethrough, whereby a quantity of said dental impression compound penetrates a number of said plurality of holes.

4. The Dental Impression Tray of claim 1, wherein said handle portion includes a lobe at an end of said handle portion distal said tray portion.

5. The Dental Impression Tray of claim 4, wherein said lobe is rotated laterally along a longitudinal axis of said handle portion at an angle from a lateral axis of said first wall toward a lateral axis of said second wall.

6. The Dental Impression Tray of claim 5, wherein said angle is about 45 degrees.

7. A dental impression tray for use in making a dental impression of a tooth with a dental impression compound, comprising:

a tray portion including a first wall and a second wall joined generally perpendicular to each other, said tray portion adapted to retain a quantity of said dental impression compound; and a handle portion extending from said tray portion, said handle portion including a lobe for grasping thereof, said lobe provided at an end of said handle portion distal said tray portion, said lobe being rotated laterally along a longitudinal axis of said handle portion at an angle from a lateral axis of said first wall toward a lateral axis of said second wall, wherein said angle of lateral rotation of said lobe is about 45 degrees.

8. The dental impression tray of claim 7, wherein said first wall and said second wall of said tray portion are positionable adjacent an occlusal surface and a buccal surface of said tooth, and wherein said tray portion is angularly removable from said buccal surface of said tooth.

9. The dental impression tray of claim 7, wherein said first wall and said second wall of said tray portion are positionable adjacent an occlusal surface and a lingual surface of said tooth, and wherein said tray portion is angularly removable from said lingual surface of said tooth.

10. The dental impression tray of claim 7, wherein said first wall and said second wall of said tray portion each have a plurality of holes therethrough for retaining a quantity of said dental impression compound.

11. A method of making a dental impression of a tooth with a dental impression compound, comprising the steps of:

(a) providing a dental impression tray comprising a tray portion including a first wall and a second wall joined generally perpendicular to each other, and a handle portion extending from said tray portion, said handle portion including a lobe at an end thereof distal said tray portion, said lobe being rotated laterally along a longitudinal axis of said handle portion at an angle of about 45 degrees from a lateral axis of said first wall toward a lateral axis of said second wall;

(b) disposing a quantity of said dental impression compound on said tray portion of said dental impression tray;

(c) positioning said tray portion of said dental impression tray adjacent a top surface and a side surface of said tooth;

(d) making said dental impression of said top surface and said side surface of said tooth with said dental impression compound; and (e) grasping said lobe of said handle portion and removing said tray portion of said dental impression tray angularly from said side surface of said tooth.

12. The method of claim 11, wherein step (c) comprises the step of positioning said tray portion of said dental impression tray adjacent an occlusal surface and a buccal surface of said tooth, wherein step (d) comprises the step of making said dental impression of said occlusal surface and said buccal surface of said tooth, and wherein step (e) comprises the step of grasping said lobe of said handle portion and removing said tray portion angularly from said buccal surface of said tooth.

13. The method of claim 11, wherein step (c) comprises the step of positioning said tray portion of said dental impression tray adjacent an occlusal surface and a lingual surface of said tooth, wherein step (d) comprises the step of making said dental impression of said occlusal surface and said lingual surface of said tooth, and wherein step (e) comprises the step of grasping said lobe of said handle portion and removing said tray portion angularly from said lingual surface of said tooth.

* * * * *